United States Patent
Jansen et al.

(12) 
(10) Patent No.: US 6,719,730 B2
(45) Date of Patent: Apr. 13, 2004

(54) SAFETY SHIELD SYSTEM FOR PREFILLED SYRINGES

(75) Inventors: Hubert Jansen, Marburg-Michelbach (DE); Samuel Gagnieux, Pont-de-Claix (FR)

(73) Assignee: Becton, Dickinson and Company, Franklin Lakes, NJ (US)

( * ) Notice: Subject to any disclaimer, the term of this patent is extended or adjusted under 35 U.S.C. 154(b) by 147 days.

(21) Appl. No.: 09/838,032

(22) Filed: Apr. 19, 2001

(65) Prior Publication Data

US 2002/0004649 A1 Jan. 10, 2002

Related U.S. Application Data

(63) Continuation-in-part of application No. 09/290,786, filed on Apr. 12, 1999, now Pat. No. 6,319,233.
(60) Provisional application No. 60/082,221, filed on Apr. 17, 1998.

(51) Int. Cl.$^7$ .................................. A61M 5/32
(52) U.S. Cl. ........................... 604/192; 604/198
(58) Field of Search ............................ 604/40, 43, 110, 604/187, 192–194, 198, 195, 263

(56) References Cited

U.S. PATENT DOCUMENTS

| | | |
|---|---|---|
| 2,801,741 A | 8/1957 | Harkness et al. |
| 2,876,770 A | 3/1959 | White .................. 128/215 |
| 4,068,661 A | 1/1978 | Hennings .............. 128/215 |
| 4,285,105 A | 8/1981 | Kirkpatrick |
| 4,361,149 A | 11/1982 | Worder ................. 128/215 |
| 4,425,120 A | 1/1984 | Sampson et al. ........ 604/198 |
| 4,573,976 A | 3/1986 | Sampson et al. ........ 604/198 |
| 4,585,445 A | 4/1986 | Hadtke |
| 4,631,057 A | 12/1986 | Mitchell |
| 4,695,274 A | 9/1987 | Fox ..................... 604/198 |
| 4,723,943 A | 2/1988 | Spencer |
| 4,723,945 A | 2/1988 | Theiling ................ 604/232 |
| 4,737,144 A | 4/1988 | Choksi |
| 4,743,233 A | 5/1988 | Schneider |
| 4,747,837 A | 5/1988 | Hauck |
| 4,758,231 A | 7/1988 | Haber et al. |
| 4,801,295 A | 1/1989 | Spencer |
| 4,804,372 A | 2/1989 | Laico et al. ............ 604/198 |
| 4,826,491 A | 5/1989 | Schramm |
| 4,840,185 A | 6/1989 | Hernandez |
| 4,850,994 A | 7/1989 | Zerbst et al. ........... 604/198 |
| 4,863,434 A | 9/1989 | Bayless |
| 4,871,355 A | 10/1989 | Kikkawa |
| 4,874,382 A | 10/1989 | Lindemann et al. ..... 604/195 |
| 4,892,521 A | 1/1990 | Laico et al. ............ 604/192 |

(List continued on next page.)

FOREIGN PATENT DOCUMENTS

| | | |
|---|---|---|
| AU | A-52050/96 | 11/1996 |
| DE | 38 23 266 C2 | 3/1989 |
| DE | 195 43 313 C2 | 6/1997 |

(List continued on next page.)

Primary Examiner—Brian L. Casler
Assistant Examiner—Kevin C Sirmons
(74) Attorney, Agent, or Firm—Hoffmann & Baron, LLP

(57) ABSTRACT

A medical injection device is provided which includes a shield system and a syringe which maybe coupled to the shield system. The shield system includes a syringe holder and a shield telescopically received in the holder and slidably coupled to the holder. A spring resiliently urges the shield from a retracted position to an extended position. Stop members are provided adjacent the distal end of the holder and the proximal end of the shield for maintaining the shield in the retracted position. The syringe is slidably coupled to the holder, and extends within the shield. Axial movement of the syringe with respect to the holder causes disengagement of the stop members, allowing the spring to move the shield to the extended position. Detents are provided on the holder for maintaining the shield in the extended position.

24 Claims, 4 Drawing Sheets

U.S. PATENT DOCUMENTS

| | | | |
|---|---|---|---|
| 4,894,055 A | 1/1990 | Sudnak | 604/198 |
| 4,897,083 A | 1/1990 | Martell | 604/192 |
| 4,900,310 A | 2/1990 | Ogle, II | |
| 4,911,693 A | 3/1990 | Paris | 604/192 |
| 4,917,673 A | 4/1990 | Coplin | |
| 4,923,445 A | 5/1990 | Ryan | |
| 4,923,447 A | 5/1990 | Morgan | 604/198 |
| 4,927,018 A | 5/1990 | Yang et al. | |
| 4,927,416 A | 5/1990 | Tomkiel | 604/198 |
| 4,932,937 A | 6/1990 | Gustavsson et al. | |
| 4,947,863 A | 8/1990 | Haber et al. | |
| 4,985,021 A | 1/1991 | Straw et al. | |
| 4,994,045 A | 2/1991 | Ranford | |
| 4,998,920 A | 3/1991 | Johnson | |
| 4,998,924 A | 3/1991 | Ranford | 604/798 |
| 5,011,479 A | 4/1991 | Le et al. | 604/198 |
| 5,019,051 A | 5/1991 | Hake | 604/198 |
| 5,024,660 A | 6/1991 | McNaughton | |
| 5,045,066 A | 9/1991 | Scheuble et al. | |
| 5,053,018 A | 10/1991 | Talonn et al. | |
| 5,057,086 A | 10/1991 | Dillard, III et al. | |
| 5,057,087 A | 10/1991 | Harmon | |
| 5,059,185 A | 10/1991 | Ryan | |
| 5,066,277 A | 11/1991 | Carrell et al. | |
| 5,067,945 A | 11/1991 | Ryan et al. | |
| 5,078,698 A | 1/1992 | Stiehl et al. | |
| 5,084,030 A | 1/1992 | Byrne et al. | |
| 5,106,379 A | 4/1992 | Leap | |
| 5,108,378 A | 4/1992 | Firth et al. | |
| RE34,045 E | 8/1992 | McFarland | |
| 5,137,521 A | 8/1992 | Wilkins | |
| 5,141,500 A | 8/1992 | Hake | |
| 5,147,303 A | 9/1992 | Martin | |
| 5,163,918 A | 11/1992 | Righi et al. | |
| 5,169,392 A | 12/1992 | Ranford et al. | |
| 5,188,614 A | 2/1993 | Hart | |
| 5,197,953 A | 3/1993 | Colonna | 604/110 |
| 5,201,708 A | 4/1993 | Martin | 604/110 |
| 5,201,720 A | 4/1993 | Borgia et al. | |
| 5,217,437 A | 6/1993 | Talonn et al. | |
| 5,226,894 A | 7/1993 | Haber et al. | |
| 5,242,240 A | 9/1993 | Gorham | 403/391 |
| 5,242,420 A | 9/1993 | Martin | 604/198 |
| 5,256,154 A | 10/1993 | Liebert et al. | |
| 5,279,581 A | 1/1994 | Firth et al. | |
| 5,300,030 A | 4/1994 | Crossman et al. | 604/136 |
| 5,300,040 A | 4/1994 | Martin | 604/198 |
| 5,304,149 A | 4/1994 | Morigi | |
| 5,308,332 A | 5/1994 | Dillard, III et al. | |
| 5,312,365 A | 5/1994 | Firth et al. | |
| 5,318,538 A | 6/1994 | Martin | 604/110 |
| 5,318,547 A | 6/1994 | Altschuler | |
| 5,338,303 A | 8/1994 | King et al. | |
| 5,338,310 A | 8/1994 | Lewandowski | |
| 5,342,309 A | 8/1994 | Hausser | |
| 5,342,320 A | 8/1994 | Cameron | |
| 5,344,407 A | 9/1994 | Ryan | |
| 5,346,480 A | 9/1994 | Hess et al. | |
| 5,348,544 A | 9/1994 | Sweeney et al. | |
| 5,350,367 A | 9/1994 | Stiehl et al. | |
| 5,352,208 A | 10/1994 | Robinson | |
| 5,356,392 A | 10/1994 | Firth et al. | |
| 5,358,491 A | 10/1994 | Johnson et al. | |
| 5,368,578 A | 11/1994 | Covington et al. | |
| 5,380,296 A | 1/1995 | Smedley et al. | |
| 5,385,555 A | 1/1995 | Hausser | |
| 5,385,557 A | 1/1995 | Thompson | |
| 5,389,085 A * | 2/1995 | D'Alessio et al. | 604/198 |
| 5,411,488 A | 5/1995 | Pagay et al. | |
| 5,411,489 A | 5/1995 | Pagay et al. | |
| 5,413,563 A | 5/1995 | Basile et al. | |
| 5,417,660 A | 5/1995 | Martin | 604/110 |
| 5,437,647 A | 8/1995 | Firth et al. | |
| 5,439,450 A | 8/1995 | Haedt | |
| 5,447,500 A | 9/1995 | Bergstresser et al. | |
| 5,458,577 A | 10/1995 | Kishigami | |
| 5,478,316 A | 12/1995 | Bitdinger et al. | 604/135 |
| 5,496,286 A | 3/1996 | Stiehl et al. | |
| 5,501,672 A | 3/1996 | Firth et al. | |
| 5,527,294 A | 6/1996 | Weatherford et al. | |
| 5,562,624 A | 10/1996 | Righi et al. | |
| 5,562,626 A | 10/1996 | Sanpietro | |
| 5,601,535 A | 2/1997 | Byrne et al. | |
| 5,611,782 A | 3/1997 | Haedt | |
| 5,616,134 A | 4/1997 | Firth et al. | |
| 5,624,400 A | 4/1997 | Firth et al. | |
| 5,647,849 A | 7/1997 | Kalin | |
| 5,658,254 A | 8/1997 | Reichenbach et al. | |
| 5,674,203 A | 10/1997 | Lewandowski | |
| 5,681,292 A | 10/1997 | Tober et al. | |
| 5,697,908 A | 12/1997 | Imbert et al. | 604/110 |
| 5,709,662 A | 1/1998 | Olive et al. | 604/135 |
| 5,713,871 A | 2/1998 | Stock | |
| 5,733,264 A | 3/1998 | Flowers | |
| 5,735,823 A | 4/1998 | Berger | |
| 5,769,822 A | 6/1998 | McGary et al. | |
| 5,769,827 A | 6/1998 | DeMichele et al. | |
| 5,776,107 A | 7/1998 | Cherif-Cheikh | |
| 5,788,677 A | 8/1998 | Botich et al. | |
| 5,792,107 A | 8/1998 | Petrocelli | |
| 5,792,122 A | 8/1998 | Brimhall et al. | |
| 5,795,336 A * | 8/1998 | Romano et al. | 604/192 |
| 5,797,885 A | 8/1998 | Rubin | |
| 5,800,395 A | 9/1998 | Botich et al. | |
| 5,800,403 A | 9/1998 | Pressly, Sr. et al. | |
| 5,800,404 A | 9/1998 | Poulsen | |
| 5,810,775 A | 9/1998 | Shaw | |
| 5,817,064 A | 10/1998 | DeMarco et al. | |
| 5,843,034 A | 12/1998 | Redfern et al. | |
| 5,843,036 A | 12/1998 | Olive et al. | 604/136 |
| 5,843,041 A | 12/1998 | Hake et al. | |
| 5,843,047 A | 12/1998 | Pyrozyk et al. | |
| 5,853,390 A | 12/1998 | Freschi | |
| 5,855,839 A | 1/1999 | Brunel | |
| 5,868,713 A | 2/1999 | Klippenstein | |
| 5,879,339 A | 3/1999 | Saito | |
| 5,882,342 A | 3/1999 | Cooper et al. | |
| 5,910,130 A | 6/1999 | Caizza et al. | 604/110 |
| 5,947,936 A | 9/1999 | Bonds | |
| 5,980,494 A | 11/1999 | Malenchek et al. | |
| 5,984,898 A | 11/1999 | Garvin | |
| 5,984,899 A * | 11/1999 | D'Alessio et al. | 604/198 |
| 5,984,906 A | 11/1999 | Bonnichsen et al. | |
| 6,004,296 A | 12/1999 | Jansen et al. | 604/198 |
| 6,010,487 A | 1/2000 | DeMichele et al. | |
| 6,017,329 A | 1/2000 | Hake | 604/198 |
| 6,030,366 A | 2/2000 | Mitchell | |
| 6,033,387 A | 3/2000 | Brunel | |
| 6,193,696 B1 | 2/2001 | Jansen et al. | 604/198 |
| 6,319,233 B1 | 11/2001 | Jansen et al. | 604/192 |

FOREIGN PATENT DOCUMENTS

| | | |
|---|---|---|
| EP | 0 467 173 A1 | 1/1994 |
| EP | 0 645 155 A2 | 3/1995 |
| EP | 0 740 942 A1 | 11/1996 |
| EP | 0 740 942 B1 | 11/1996 |
| EP | 0 864 335 A2 | 9/1998 |
| EP | 0740942 | 8/1999 |
| EP | 0966983 | 12/1999 |
| EP | 1090652 | 4/2001 |
| WO | WO 92/19296 | 11/1992 |

| WO | WO 97/02855 | 1/1997 |
| WO | WO 97/14455 | 4/1997 |
| WO | WO 98/26824 | 6/1998 |
| WO | WO 98/26825 | 6/1998 |
| WO | WO 98/35714 | 8/1998 |
| WO | WO 99/16489 | 4/1999 |
| WO | WO 99/22791 | 5/1999 |
| WO | WO 99/37343 | 7/1999 |
| WO | WO 99/59658 | 11/1999 |
| WO | 0130427 | 5/2001 |

* cited by examiner

SAFETY SHIELD SYSTEM FOR PREFILLED SYRINGES

CROSS REFERENCE TO RELATED APPLICATIONS

This application is a continuation-in-part of Ser. No. 09/290,756 now Pat. No. 6,319,233 filed Apr. 12, 1999, which application claims priority under 35 U.S.C. §119(e) to U.S. provisional patent application Ser. No. 60/082,221 filed Apr. 17, 1998.

BACKGROUND OF THE INVENTION

1. Field of the Invention

The field of the invention relates to shield systems for protecting against needle sticks, and syringes including such systems.

2. Brief Description of the Related Art

Syringes are well known medical devices for administering medicaments, drugs and vaccines to patients. Prefilled syringes are generally considered as those which are filled with a selected dosage of medicament, drug or vaccine by a pharmaceutical manufacturer for distribution to the end user. They are often comprised of a glass or plastic barrel which contains the medicament, drug or vaccine, and a stopper slidably mounted within the barrel. The distal end of the barrel includes a needle cannula or the like affixed thereto or a connector for a needle cannula assembly such as a Luer fitting. The proximal end of the syringe is open to allow the insertion of a stopper of a plunger assembly. The plunger and stopper assembly allows the user to apply manual force to the plunger, causing the medicament, drug or vaccine to be delivered through the needle cannula or other piercing element.

The use of a sharp-pointed piercing element entails the risk of an accidental needle stick. To avoid such accidents, many prior art hypodermic syringes have included rigid cylindrical safety shields telescoped over the syringe barrel. These shields can be moved between a retracted position where the needle is exposed for use, to an extended position where the needle is surrounded by the shield. U.S. Pat. Nos. 4,425,120, 4,573,976, 4,850,994 and 4,923,447 disclose various shield systems for hypodermic syringes. The latter two patents disclose shields which may be spring-actuated. It is ordinarily desirable to lock the needle shields in the protected positions, and a number of prior art designs provide for such locking. Some systems, such as those disclosed in U.S. Pat. Nos. 5,201,708, 5,242,240 and 5,318,538 are designed to allow the shields to be retracted from their locked, extended positions.

A shield system for protecting the piercing element of a prefilled syringe is also disclosed in European Publication No. EP 0 740 942 A1. The disclosed system includes a holder which is coupled to the flange of the syringe barrel, and a shield which is telescopically mounted to the holder. Two hands are required to operate this system.

SUMMARY OF THE INVENTION

This invention relates to a safety shield system for a syringe, medical cartridge or the like and such a system as used in combination with an assembly capable of functioning as a syringe. In accordance with the preferred embodiment of the system, the user is able to cause the shielding of a needle cannula by simply applying additional pressure to the plunger rod of the syringe following injection of the contents of the syringe barrel. The shield may accordingly be deployed automatically through the use of only one hand. As there is no need to place the hand near the needle for any purpose, the risk of needle stick injury is further reduced.

In accordance with the objects of the invention, a medical device is provided which includes an automatically operable shield system mounted to a syringe barrel. The system includes a tubular holder which defines an enclosure. A tubular needle shield is slidably attached to the holder and preferably telescopically received within the holder. The syringe barrel is received within the holder and shield assembly, preferably within the tubular shield, and the shield is extendable from a retracted position, wherein the needle cannula is exposed to an extended position, wherein the shield encloses the needle cannula following injection. A partially compressed spring is located within the holder and shield assembly which biases the shield axially toward the extended position. The shield includes a stop member adjacent its proximal end and the holder includes a stop member adjacent its distal end which retains the shield in its retracted position. In the preferred embodiment, the stop member on the holder is an annular internal groove adjacent the distal end of the holder and the stop member on the shield is a radially outwardly extending annular rib. In the most preferred embodiment, the shield includes a further stop member in the form of a second radial rib adjacent the proximal end of the shield which engages the stop member on the holder when the shield is extended to its extended position. The force of the partially compressed spring by itself is insufficient to disengage the stop member adjacent the distal end of the shield and the stop member on the holder. However, axial movement of the syringe following injection further compresses the spring, disengaging the stop members and releasing the shield. with respect to the holder between retracted and extended positions. It is intended to cover the needle tip when in the extended position. The syringe barrel is operably coupled to the shield such that sufficient axial movement of the syringe barrel causes axial displacement of the shield sufficient to cause disengagement of the stop members. Such movement of the barrel is ordinarily caused by pressure on the plunger rod of the syringe, driving the stopper against the end of the barrel following complete injection of the contents of the barrel. Upon disengagement of the first and second stop members, the spring causes the shield to move to the extended position.

The proximal end of the holder is preferably adapted to engage and retain the syringe flange upon receipt of the syringe barrel through the proximal end of the holder. The axial or distal movement of the shield is preferably limited by a second abutment surface or rib adjacent the proximal end of the shield which engages a radially inwardly projecting distal end portion of the holder. Such movement could alternatively be limited by a tether connecting the holder and shield. The shield is preferably positioned within the holder such that the spring engages a stop member extending radially outwardly from the shield. The opposite end of the spring can bear against any suitable surface, operably connected to the holder, such as the flange on the syringe barrel, if present, or a collar portion of an end fitting slidably positioned within the holder.

The shield system according to the invention is comprised of a holder, a shield, a spring and, preferably an end fitting. The tubular shield is adapted for receiving a syringe. The shield is slidably mounted to the holder, and is movable between a retracted position, wherein the shield needle cannula is exposed and an extended position wherein the needle cannula is enclosed. A spring urges the shield towards the extended position. The holder includes a stop member which is engageable with a first stop member of the shield to maintain it in the retracted position. Sufficient axial movement of the shield causes disengagement of the stop member, allowing the spring to move the shield to the extended position. The holder is engageable with a second portion of the shield axially-spaced from the first portion to prevent decoupling of the shield and holder when the shield moves to the extended position. An end fitting is preferably incorporated in the system to maintain the position of the spring prior to insertion of a syringe into the holder.

The shield system facilitates the safe use of prefilled syringes, though it can be adapted for other sharp-pointed injection devices, such as syringes filled just before use, as well. When employed with a syringe, the system allows the contents of the syringe to be expressed in a conventional manner. Continued, and preferably increased pressure on the plunger rod following injection causes the syringe barrel to move axially, thereby axially displacing the shield. Such displacement causes release of the stop member, and the spring to move the shield over the needle of the syringe. Protection against needle sticks is accordingly provided.

DETAILED DESCRIPTION OF THE INVENTION

An injection device 10 for injecting a medicament, drug or vaccine into a patient is shown in FIGS. 1–8. The device comprises a prefilled or prefillable syringe 12 and a shield assembly 14 coupled to the syringe.

Figure 2:
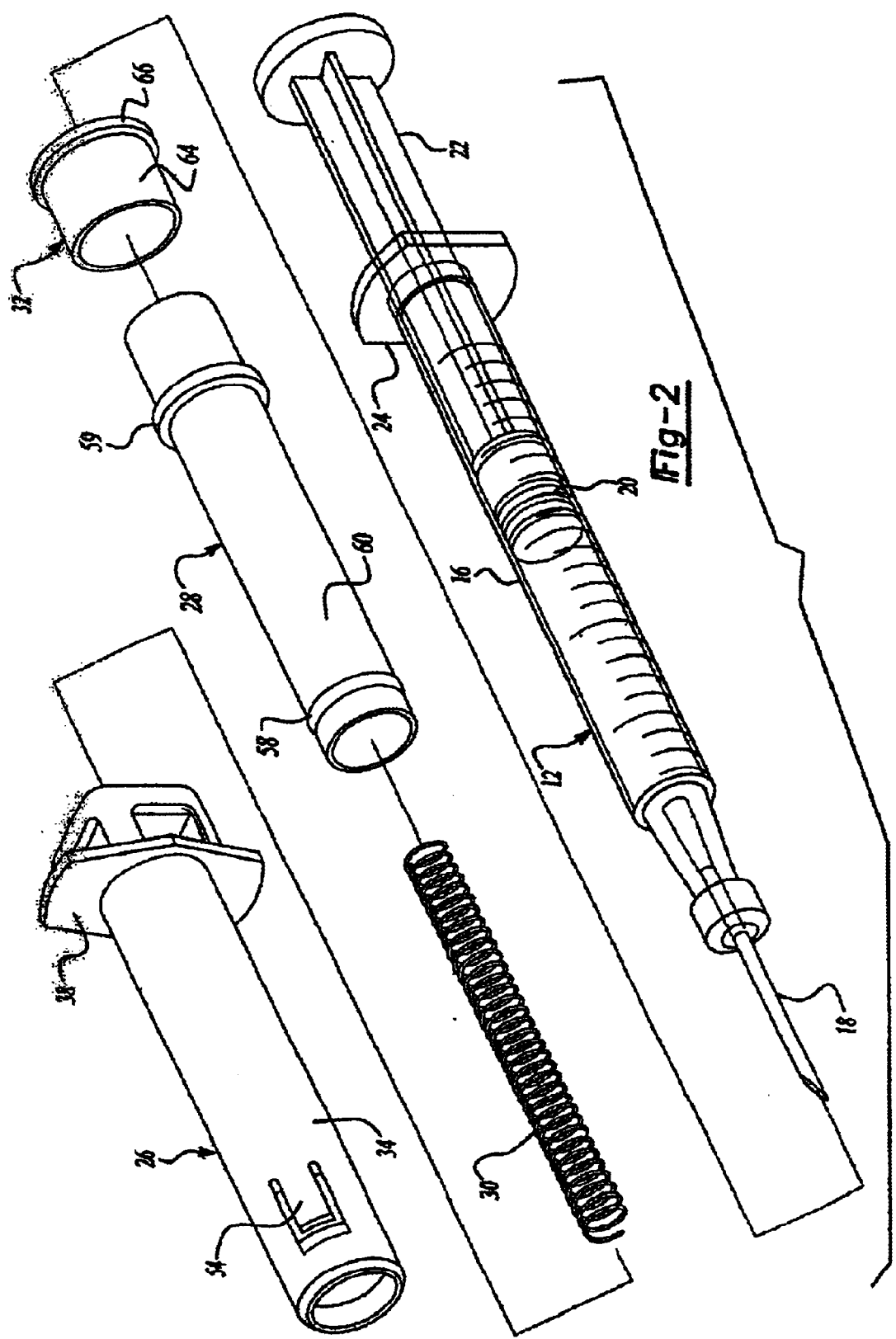
FIG. 2 is an exploded, perspective view thereof.

Syringes are ordinarily comprised of a generally cylindrical portion, known as a barrel, a needle cannula or other piercing element or a connecting element secured to one end of the barrel, and a piston or stopper slidably positioned within the barrel. The needle cannula may be removably secured to the barrel, but is more likely to be permanently secured to the barrel when the barrel is comprised of glass. Glass barrels are commonly used in prefillable syringes, and ordinarily contain a single dose of medication. Prefilled syringes made from plastic are also known to the art. Referring to FIG. 2, the shield system 14 disclosed herein is employed in conjunction with a prefillable syringe 12 including a barrel 16, a cannula such as a needle 18 permanently secured to the barrel, a stopper 20 slidably positioned with the barrel, and a plunger rod 22 engageable with the stopper. The syringe barrel 16 includes a radially outwardly extending integral flange 24, which is used to couple the syringe to the shield system.

The shield system 14 according to this invention includes a tubular holder 26, a tubular shield 28 coupled to the holder, and a coil spring 30. It also preferably includes a holder end fitting 32 which engages one end of the spring. With the exception of the spring, all of the components of the system may be made from a semi-rigid plastic material, such as polypropylene. The spring is preferably a metal coil spring.

The holder 26 is preferably comprised of an elongate, generally cylindrical tubular body 34 which defines a generally cylindrical enclosure. The holder has proximal and distal open ends 35 and 37, respectively, which provide access to the enclosure. A flange 38 extends radially outwardly from the holder body near the proximal open end 35 thereof. The flange and body of the holder are designed for easy handling as an injection is made. Only one hand should be required for injection.

Figure 1:
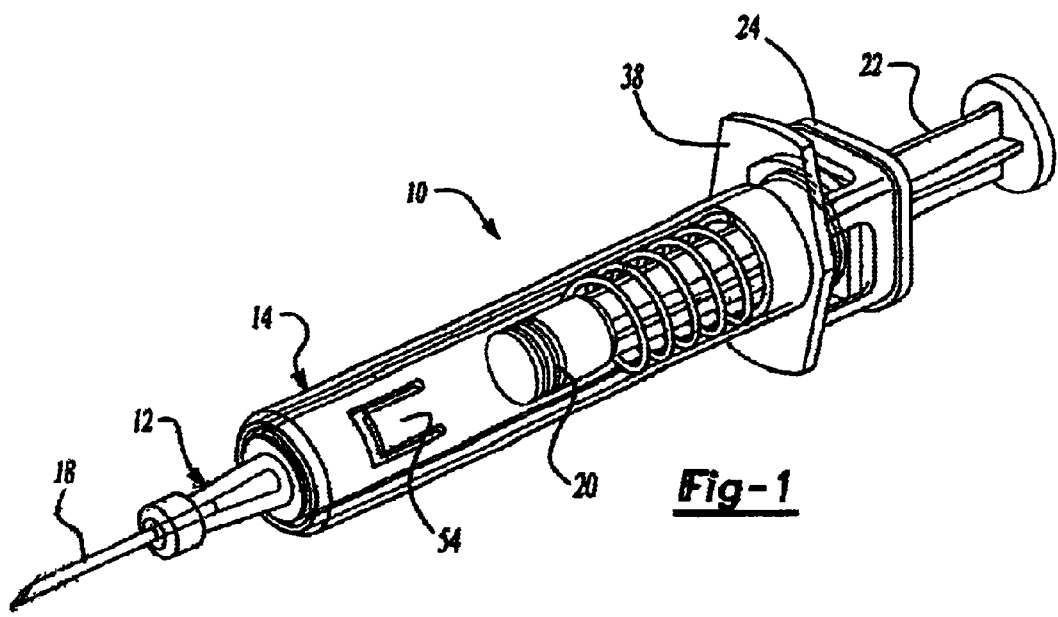
FIG. 1 is a top perspective view of a preferred embodiment of the medical device according to the invention as assembled.
Figure 3:
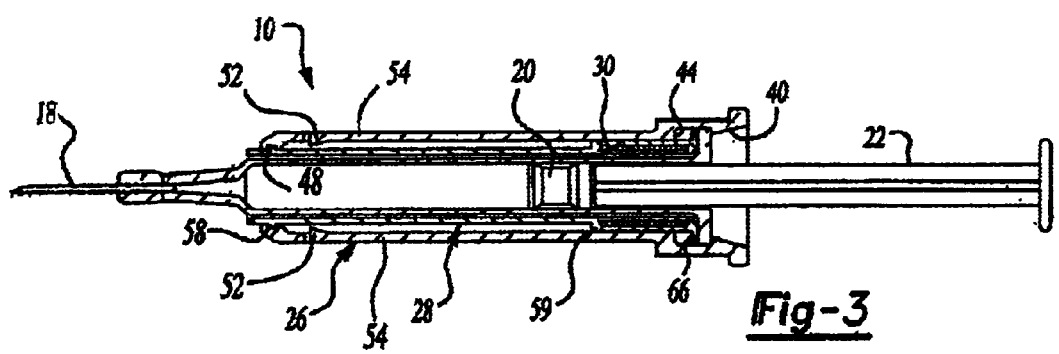
FIG. 3 is a sectional elevation view thereof.
Figure 4:
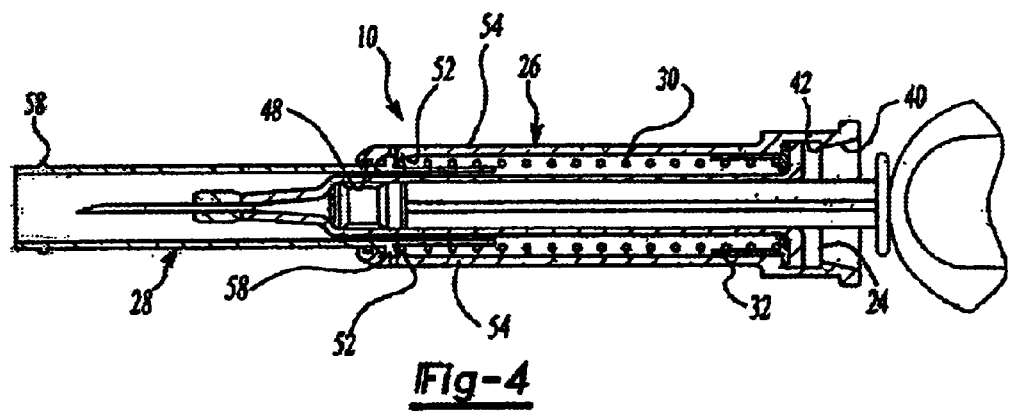
FIG. 4 is a sectional view thereof following actuation of the shield system of the device.
Figure 5:
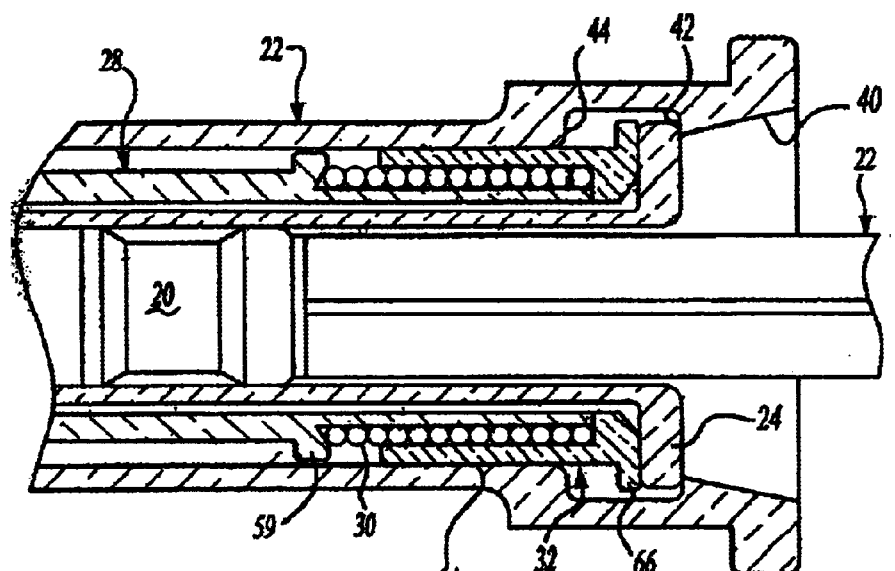
FIG. 5 is an enlarged sectional view of the proximal portion of the device prior to actuation of the shield system.

The inner surface of the holder enclosure includes a frustoconical surface 40 adjoining the proximal open end 35 as shown in FIGS. 3 and 5. A first abutment surface 42 is formed at the inner end of this surface, as shown in FIGS. 4 and 5. A second abutment surface 44 is formed by the holder body in opposing spaced relation to the first abutment surface. As described below, the axial spacing between these abutment surfaces 42 and 44 corresponds, though may not be equal to the axial distance which the syringe can move with respect to the holder. The inner diameter of the holder, measured at the abutment surfaces, is smaller than the distance between the edges or major diameter of the syringe flange 24. Accordingly, once the syringe is inserted far enough into the holder such that the flange 24 is located between abutment surfaces 42, 44, it is slidably coupled to the holder. The spring 30 urges the syringe flange 24 towards engagement with the first abutment surface 42 as shown in FIG. 5.

Figure 6:
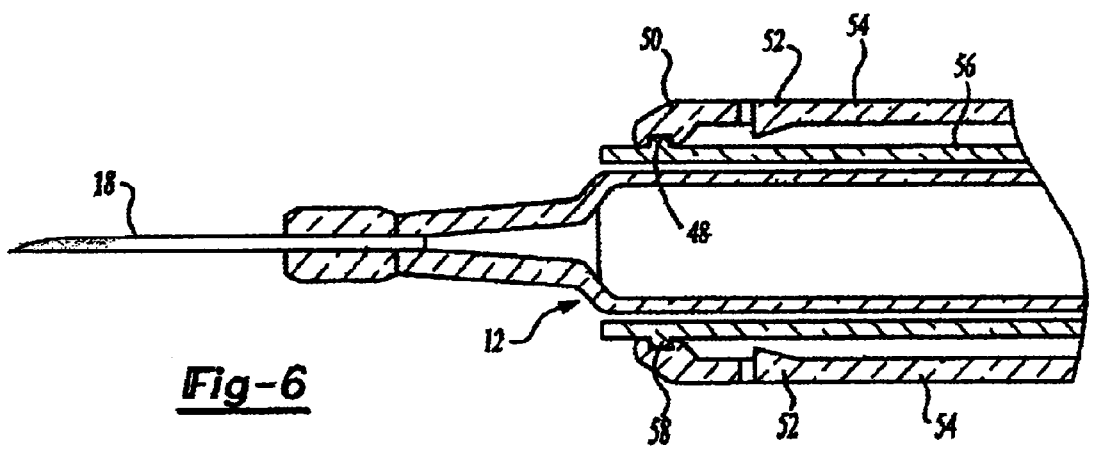
FIG. 6 is an enlarged sectional view showing a portion of the device, including the distal portion of a syringe holder of the device, prior to actuation of the shield system.
Figure 7:
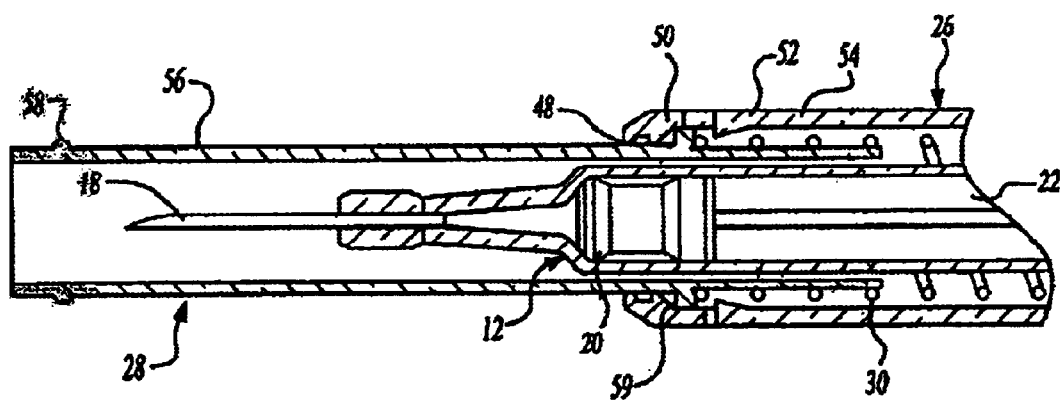
FIG. 7 is an enlarged sectional view showing a portion of the device including the distal portion of the syringe holder following actuation of the shield system.

A radial groove 48, as best shown in FIGS. 6 and 7, is provided on the inside surface of the holder adjacent its distal end 37. The radial groove is provided in an arcuately inwardly projecting distal end portion 50 of the holder, which also serves as a stop member as described below.

A pair of opposed detents 52 are provided on the holder which prevent retraction of the shield 28 once extended. Each of these detents 52 is formed on an axially extending arm 54 which is integral with the holder body 34 and pivotable with respect thereto. (See FIGS. 2, 6 and 7.) The end surface of each detent 52 faces the distal open end 37 of the holder which is substantially perpendicular to the longitudinal axis of the holder. An inclined end surface 53 is provided on the opposite side of each detent, and faces the proximal open end 37.

The shield 28 is comprised of a substantially cylindrical tubular body 56. The tubular shield 28 preferably has an outside diameter small enough to be positioned within the holder and an inside diameter large enough to receive the barrel 16 of the syringe. As shown in FIGS. 2 and 7, a stop member 58 in the form of a radially outwardly extending collar or rib is formed integrally on the body 56 of the shield near the distal end thereof. A second, radially outwardly extending collar or rib is formed integrally on the shield body 56 towards the proximal end, and defines another stop member 59. The second collar 59 is preferably larger in diameter than the first collar.

The coil spring 30 has an internal diameter large enough to fit over the proximal end of the shield, such that one end thereof bears against the collar 59. The opposite end of the spring bears against the collar 66 of the holder end fitting 32 as shown in FIG. 5.

The spring 30 causes the shield 28 to move axially upon axial movement of the plunger rod 22 if the spring is further compressed when the shield is in the retracted position. Direct engagement of the end fitting 32 or syringe flange 24 and shield, as provided in the preferred embodiment, is not necessary in such an arrangement. The operation of the device can be effected whether the shield, spring, end fitting and syringe barrel are directly or indirectly engaged, so long as axial movement of the syringe barrel causes axial movement of the shield. As discussed below, the use of an end fitting is preferred, but optional.

Figure 8:
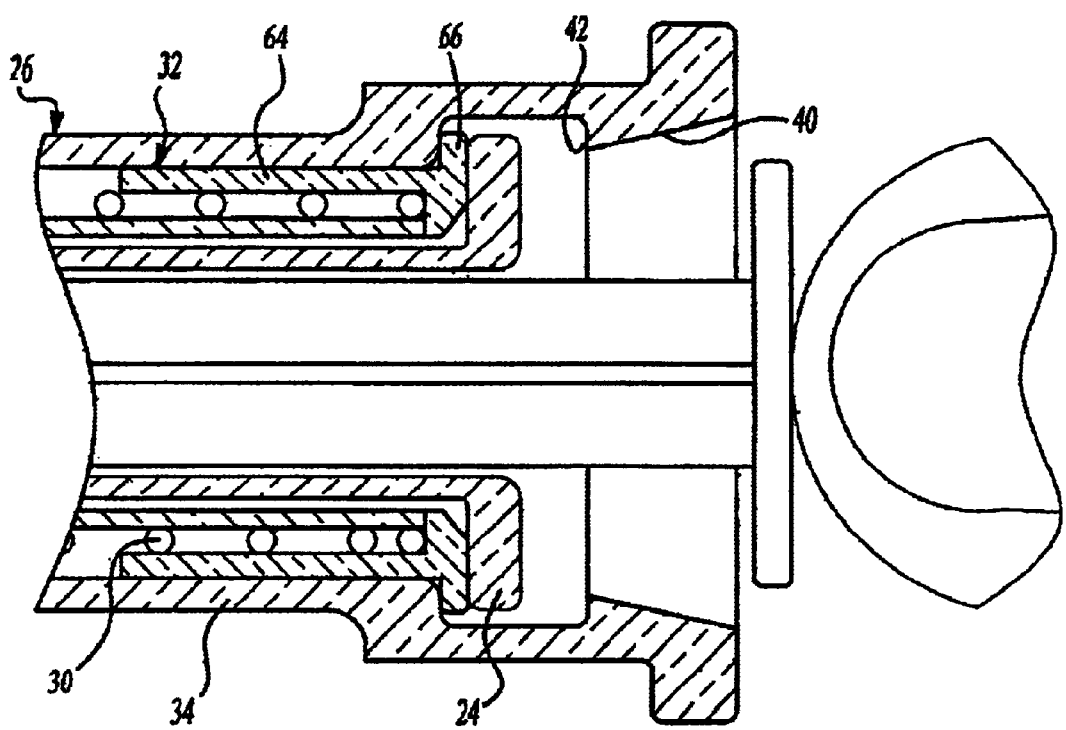
FIG. 8 is an enlarged sectional view of the proximal portion of the device following actuation of the shield system.

The end fitting 32 includes a cylindrical tubular body 64 which can be inserted within the body 34 of the holder as shown in FIG. 8. One end of the spring 30 is insertable within the end fitting. An annular wall or collar 66 is provided at one end of the cylindrical body 64, and is preferably integral therewith. This collar 66 extends radially outwardly and radially inwardly with respect to the cylindrical body 64. The radially outwardly extending portion of the collar 66 is adapted to engage the first abutment surface 42 in the holder, prior to receipt of the collar so that it can be snapped behind the frustoconical portion 40 at the proximal end 35 of the holder. It is used to maintain the spring 30 in position within the holder, thereby allowing the shield system to be manufactured as an assembly which does not include the syringe. The radially inwardly extending portion of the collar 66 is adapted to engage between the first end of the spring 30 and the syringe flange 24 as shown in FIG. 5. The holder end fitting 32 will accordingly protect this flange from direct contact with the spring 30. Such protection is desirable where the shield system is used in conjunction with a glass syringe in order to prevent breakage. In the absence of the optional end fitting 32, the first abutment surface 42 retains the syringe within the holder by engaging the syringe flange 24 directly. The particular structure of the retaining member or members is not critical so long as the syringe 12 remains slidably coupled to the holder 26 during use of the device. Axial movement of the syringe 12 causes corresponding axial movement of the end fitting 32 further compressing the spring 30 until the inwardly extending portion of the annular collar 66 engages the abutment surface 44. In the absence of the end fitting, the syringe flange 24 would engage this surface directly.

The assembly and use of this preferred embodiment of the invention will now be described. The shield 28 is slidably mounted to the holder 26 by inserting the shield through the proximal open end 35 thereof until the first stop member or collar 58 is received in the radial groove or stop member 48 in the holder. The spring is inserted through the proximal open end 35 of the holder, and over the shield until it abuts the relative large collar or rib 59. As a final step, prior to providing the shield system to the end user, the end fitting 32 is slipped over the exposed end of the spring and pushed through the proximal end 35 of the holder. The spring is substantially but not fully compressed during this step. The shield 28 is resiliently urged towards the distal end 37 of the holder 26 while the end fitting 32 is urged towards the proximal end thereof by the coil spring 30. Neither element can move due to the engagement of the stop members 48, 58, and the annular wall or collar 66 of the end fitting with the first abutment surface 42, respectively. The force of the partially compressed spring 30 is insufficient to cause the disengagement of the shield and holder.

The shield system 14 receives a syringe 12 of appropriate size through the proximal open end 35 of the holder. The system as shown is designed for receiving a syringe including a flange. The syringe flange engages the conical surface 40 and is inserted into the shield until the flange 24 snaps behind the first abutment surface 42 in the holder. The end fitting 32 is displaced axially slightly during this procedure. As the needle of the syringe is ordinarily protected by a needle cover or cap (not shown) at this time, it may be safely coupled to the shield system.

The force required to disengage the rib or stop 58 of the shield from the stop member or internal groove 48 of the holder is greater than the force of the spring plus the force required to expel the contents of the syringe barrel 16 by compressing the stopper 20. The plunger rod is employed to move the stopper 20 through the syringe barrel until the contents of the barrel have been completely expelled. (The needle cover is, of course, removed prior to injection.) The contents of the barrel of a prefilled syringe ordinarily correspond to a single dose of the prescribed medicament.

Following removal of the needle 18 from the patient, the user applies a greater force to the plunger rod 22 than that applied during injection. Such force causes axial displacement of the end fitting 32, the spring 30 and the shield 28 with respect to the holder 28. The distance between the annular wall or collar 66 of the end fitting (or the flange 24) is then sufficient to permit the second stop member rib 58 to move far enough axially to where its retention by the groove 48 is overcome by the force of the spring. The first stop member 48 may also be displaced radially inwardly as such sliding occurs if sufficient flexibility of the holder body is provided.

Once the rib 58 and groove 48 are disengaged, the spring 30 expands rapidly, causing the shield 28 to slide axially or distally with respect to the holder 26 and syringe barrel. The collar or stop member 59 moves past the detents 54, causing them to deflect radially outwardly and then inwardly to their original positions. The collar 59 then engages the abutment surface 50 as shown in FIG. 7. Upon such engagement, the needle cannula 18 is entirely and permanently enclosed and covered by the shield 28, as shown in FIGS. 4 and 7. The shield cannot be retracted sufficiently to expose the needle tip due to the engagement of the stop member or collar 59 with the detents 52. It cannot be removed from the holder as the stop member 59 cannot move past the abutment surface 52.

The above-described procedure is particularly safe as it can be accomplished using only one hand. No second hand is required to move the shield, push a button or use any other actuating member to release the shield spring. The risk of accidental actuation of the shield through inadvertent contact with an actuating button is also eliminated. Moreover, a one-handed system is simpler for most people to use. It is readily apparent that the shield system can be adapted for use with syringes of various shapes and sizes without major modification.

The deployment of a shield in response to the axial displacement of a syringe barrel with respect to a holder is a safe and effective way of protecting against needle sticks. The preferred embodiment of the invention, as described above, provides advantages for the user as well as the manufacturer. The components are relatively easy to manufacture and assemble. It will be appreciated, however, that modifications can be made without changing the basic mode of operation of the device. For example, the stop member 58, of the shield, rather than being in the form of a collar, can simply be the end of the shield. The dimensions of each component of the medical device are determined by the specific uses(s) for which it is designed.

It will be appreciated and understood by those skilled in the art that further and additional revisions to the invention may be devised without departing from the spirit and scope of the appended claims, the invention not being limited to the specific embodiment shown.

What is claimed is:

1. A shield system comprising:
   a holder comprising an elongate body, an elongate enclosure defined by said body, and said holder including proximal and distal open ends;
   an elongate tubular shield coupled to said holder and positioned at least partially within said holder enclosure, said shield including open proximal and distal ends and a passage extending therethrough, and said shield being slidable within said holder enclosure between a retracted position and an extended position wherein said shield extends beyond said distal open end of said holder;
   a spring at least partially compressed located within said enclosure operably biased between said holder and said shield and urging said shield towards said extended position;
   a stop member on said holder adjacent said distal open end and engageable with said shield, said stop member maintaining said shield in said retracted position against the compressive force of said spring and releasing said shield upon sufficient axial displacement of said shield; and
   a detent mounted to said holder and engageable with said shield when said shield is in said extended position preventing retraction of said shield from said extended position.

2. A shield system as defined in claim 1, wherein said shield includes a radially outwardly extending stop member engageable with said first detent.

3. A shield system as defined in claim 2, wherein said detent being located adjacent said distal open end of said holder and being axially spaced from said stop member, said stop member of said shield being movable past said resilient detent upon movement of said shield to said extended position and engageable with said detent preventing uncoupling of said shield from said holder, said stop member of said shield being engageable with said detent upon movement of said shield from the extended position towards the retracted position.

4. A system as defined in claim 3, wherein said shield includes a second radially outwardly extending stop member adjacent said proximal end of said shield engageable with said stop member on said holder.

5. A system as defined in claim 4, wherein said further radially extending stop member is smaller in diameter than said stop member which is engageable with said detent.

6. A shield system for an injection device, comprising:
   a holder defining an enclosure within which a cylindrical barrel may partially extend, the cylindrical barrel being axially movable with respect to said holder;
   a shield operably connected to said holder and being axially movable with respect to said holder between a retracted position, wherein said shield is at least partially within said holder; and an extended position, wherein said shiled is at least partially outside of said holder;
   a spring partially compressed within said holder and operably positioned between said holder and said shield so as to bias said shield towards said extended position;
   a first stop member on said shield;
   a second stop member on extending radially inwardly from an internal surface of said holder adjacent a distal end of said holder, said sceond stop member being engageable with said first stop member when said shield is in said retracted position, the force of said spring being insufficient to cause disengagement of said first and second stop members; and
   a third stop member on said shield distally spaced from said first stop, said third stop member being larger in diameter than said first stop member; wherein the barrel is operationally coupled to said shield such that sufficient axial movemnet of the barrel causes axial movement of said shield relative to said holder causing disengagement of said first and second stop members, said spring then driving said shield to said extended position.
   a spring partially compressed within said holder and operably positioned between said holder and said shield so as to bias said shield towards said extended position;
   a first stop member on said shield;
   a second stop member on extending radially inwardly from an internal surface of said holder adjacent a distal end of said holder, said sceond stop member being engageable with said first stop member when said shield is in said retracted position, the force of said spring being insufficient to cause disengagement of said first and second stop members; and
   a third stop member on said shield distally spaced from said first stop, said third stop member being larger in diameter than said first stop member; wherein the barrel is operationally coupled to said shield such that sufficient axial movemnet of the barrel causes axial movement of said shield relative to said holder causing disengagement of said first and second stop members, said spring then driving said shield to said extended position.

7. A shield system as defined in claim 6, further comprising:
   a substantially cylindrical barrel having a needle cannula connected to an end thereof;
   wherein said needle cannula is exposed and extends beyond an end of said holder when said shield is in said retracted position, and said needle cannula is enclosed by said shiedl when said shield is in said extended position.

8. A shield system as defined in claim 7, wherein said shield is positioned at least partially within said holder, said holder comprising an elongate, generally tubular body including a detent ans said second stop member when said shield is in the extended position, and said detent preventing said shield from being retracted from said extended position and exposing said needle cannula.

9. A shield system as defined in claim 8, wherein said detent is radially deflectable with respect to said holder.

10. A shield system as defined in claim 7, wherein said barrel includes a flange, said flange being slidably retained by said holder.

11. A shield system as defined in claim 6 wherein said shield is telescopically received within said holder and said first stop member extending radially outwardly from said shield.

12. A shield system as defined in claim 6, wherein said first stop member is adjacent a distal end of said shield.

13. A shield system as defined in claim 6, including an end fitting slidably mounted to said holder and engaging a proximate end of said barrel.

14. A shield system as defined in claim 6, wherein said holder comprises an elongate, generally tubular body having proximal and distal end portions, said proximal end portion including a radially outwardly extending flange, said distal end portion including said second stop member.

15. A shield system for an injection device, comprising:
   a holder defining an enclosure within which a cylindrical barrel may partially extend, the cylindrical barrel being axially movable with respect to said holder, said holder including an elongate, generally tubular body having proximal and distal end portions, said proximal end portion including a radially outwardly extending flange;
   a shield operably connected to said holder and being axially movable with respect to said holder between a retracted position, wherein said shield is at least partially within said holder, and an extended position, wherein said shield is at least partially outside of said holder,
   a spring partially compressed within said holder and operably positioned between said holder and said shield so as to bias said shield towards said extended position;
   a first stop member on said shield;
   a second stop member on said distal end portion of said body of said holder and engageable with said first stop member when said shield is in said retracted position, the force of said spring being insufficient to cause disengagement of said first and second stop members; and
   a third stop member on said shield spaced from said first stop member;
   wherein the barrel is operationally coupled to said shield such that sufficient axial movement of the barrel causes axial movement of said shield relative to said holder causing disengagement of said first and second stop members, said spring then driving said shield to said extended position.

16. A shield syste, as defined in claim 15, further comprising:
   a substantially cylindrical barrel having a needle cannula connected to an end thereof;
   wherein said needle cannula is exposed and extends beyond an end of said holder when said shield is in said retracted position, and said needle cannula is enclosed by said shield when said shield is in said extended position.

17. A shield system as defined in claim 16, wherein said shield is positioned at least partially within said holder, said holder comprising an elongate, generally tubular body including a detent engageable with said third stop member, said third stop member being positionable between said detent and said second stop member when said shield is in the extended position, and said detent preventing said shield from being retracted from said extended position and exposing said needle cannula.

18. A shield system as defined in claim 17, wherein said detent is radially deflectable with respect to said holder.

19. A shield system as defined in claim 16, wherein said barrel includes a flange, said flange being slidably retained by said holder.

20. A shield system as defined in claim 15 wherein said shield is telescopically received within said holder and said first stop member extending radially outwardly from said shield.

21. A shield system as defined in claim 15 wherein said second stop member extends radially inwardly from an internal surface of said holder.

22. A shield system as defined in claim 21, wherein said first stop member is adjacent a distal end of said shield.

23. A shield system as defined in claim 21, wherein said third stop member is larger in diameter than said first stop member.

24. A shield system as defined in claim 15, including an end fitting slidably mounted to said holder and engaging a proximate end of said barrel.

* * * * *

UNITED STATES PATENT AND TRADEMARK OFFICE
CERTIFICATE OF CORRECTION

PATENT NO. : 6,719,730 B2
DATED : April 13, 2004
INVENTOR(S) : Jansen et al.

It is certified that error appears in the above-identified patent and that said Letters Patent is hereby corrected as shown below:

Column 1,
Lines 7-8, delete "...Ser.No. 09/290,756 now Pat. No..." and insert -- Ser. No. 09/290,786 now Pat. No. --.

Column 7,
Line 63, delete "...said shiled is at least partially..." and insert -- said shield is at least partially --.

Column 8,
Line 4, delete "...said sceond stop member..." and insert -- said second stop member --.
Line 33, delete "...axial movement of the barrel..." and insert -- axial movement of the barrel --.
Line 45, delete "including a detent ans said second stop member" and insert -- including a detent engageable with said third stop member, said third stop member being positionable between said detent and said second stop member --.

Column 10,
Line 1, delete "...A shield syste, as defined in..." and insert -- A shield system as defined in... --.

Signed and Sealed this

Thirteenth Day of July, 2004

JON W. DUDAS
*Acting Director of the United States Patent and Trademark Office*

UNITED STATES PATENT AND TRADEMARK OFFICE
CERTIFICATE OF CORRECTION

PATENT NO. : 6,719,730 B2
DATED : April 13, 2004
INVENTOR(S) : Jansen et al.

It is certified that error appears in the above-identified patent and that said Letters Patent is hereby corrected as shown below:

Column 1,
Lines 7-8, delete "...Ser.No. 09/290,756 now Pat. No…" and insert -- Ser. No. 09/290,786 now Pat. No. --.

Column 7,
Line 63, delete "…said shiled is at least partially…" and insert -- said shield is at least partially --.

Column 8,
Line 4, delete "...said sceond stop member…" and insert -- said second stop member --.
Line 33, delete "…axial movement of the barrel…" and insert -- axial movement of the barrel --.
Line 45, delete "...by said shiedl when said shield.." and insert -- by said shield when said shield --.
Line 50, delete "including a detent ans said second stop member" and insert -- including a detent engageable with said third stop member, said third stop member being positionable between said detent and said second stop member --.

Column 10,
Line 1, delete "...A shield syste, as defined in…" and insert -- A shield system as defined in… --.

This certificate supersedes Certificate of Correction issued July 13, 2004.

Signed and Sealed this

Twenty-second Day of February, 2005

JON W. DUDAS
*Director of the United States Patent and Trademark Office*

UNITED STATES PATENT AND TRADEMARK OFFICE
CERTIFICATE OF CORRECTION

| | |
|---|---|
| PATENT NO. | : 6,719,730 B2 |
| APPLICATION NO. | : 09/838032 |
| DATED | : April 13, 2004 |
| INVENTOR(S) | : Hubert Jansen and Samuel Gagnieux |

It is certified that error appears in the above-identified patent and that said Letters Patent is hereby corrected as shown below:

Col. 7, Line 54 – Col. 8, Lines 1-37, Claim 6 To Read:

6. A shield system for an injection device, comprising:

a holder defining an enclosure within which a cylindrical barrel may partially extend, the cylindrical barrel being axially movable with respect to said holder;

a shield operably connected to said holder and being axially movable with respect to said holder between a retracted position, wherein said shield is at least partially within said holder; and an extended position, wherein said shield is at least partially outside of said holder;

a spring partially compressed within said holder and operably positioned between said holder and said shield so as to bias said shield towards said extended position;

a first stop member on said shield;

a second stop member on extending radially inwardly from an internal surface of said holder adjacent a distal end of said holder, said second stop member being engageable with said first stop member when said shield is in said retracted position, the force of said spring being insufficient to cause disengagement of said first and second stop members; and

UNITED STATES PATENT AND TRADEMARK OFFICE
CERTIFICATE OF CORRECTION

PATENT NO. : 6,719,730 B2
APPLICATION NO. : 09/838032
DATED : April 13, 2004
INVENTOR(S) : Hubert Jansen and Samuel Gagnieux It is certified that error appears in the above-identified patent and that said Letters Patent is hereby corrected as shown below:

a third stop member on said shield distally spaced from said first stop, said third stop member being larger in diameter than said first stop member; wherein the barrel is operationally coupled to said shield such that sufficient axial movement of the barrel causes axial movement of said shield relative to said holder causing disengagement of said first and second stop members, said spring then driving said shield to said extended position.

Signed and Sealed this

Twenty-third Day of December, 2008

JON W. DUDAS
*Director of the United States Patent and Trademark Office*